(12) United States Patent
Draper et al.

(10) Patent No.: US 11,116,906 B2
(45) Date of Patent: *Sep. 14, 2021

(54) ARRANGEMENT FOR DETECTING A POSITION OF A PLUNGER

(71) Applicant: Sanofi-Aventis Deutschland GMBH, Frankfurt am Main (DE)

(72) Inventors: Paul Richard Draper, Worcestershire (GB); Anthony Paul Morris, Coventry (GB); Stephen Francis Gilmore, Bristol (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/727,003

(22) Filed: Dec. 26, 2019

(65) Prior Publication Data

US 2020/0155762 A1    May 21, 2020

Related U.S. Application Data

(63) Continuation of application No. 15/877,920, filed on Jan. 23, 2018, now Pat. No. 10,561,790, which is a (Continued)

(30) Foreign Application Priority Data

Jan. 29, 2013   (EP) .................................. 13153137

(51) Int. Cl.
*A61M 5/20* (2006.01)
*G01D 5/34* (2006.01)
(Continued)

(52) U.S. Cl.
CPC ............ *A61M 5/20* (2013.01); *A61M 5/1452* (2013.01); *A61M 5/3146* (2013.01); *G01D 5/32* (2013.01);
(Continued)

(58) Field of Classification Search
CPC ......... G01D 5/32; G01D 5/34; A61M 5/1452; A61M 5/20; A61M 5/3146;
(Continued)

(56) References Cited

U.S. PATENT DOCUMENTS

| 533,575 A | 2/1895 | Wilkens |
| 5,106,379 A | 4/1992 | Leap |

(Continued)

FOREIGN PATENT DOCUMENTS

| CN | 1245888 | 3/2000 |
| CN | 1486198 | 3/2004 |

(Continued)

OTHER PUBLICATIONS

English Translation of Abstract of PCT Patent Application No. WO 2011/0995512, dated Nov. 2, 2017, 2 pages.
(Continued)

*Primary Examiner* — Sang H Nguyen
(74) *Attorney, Agent, or Firm* — Fish & Richardson P.C.

(57) ABSTRACT

The invention relates to an arrangement for detecting a position of a plunger (4) relative to a bung (3) in a drug cartridge (1), comprising a proximity sensor (5) located close to a distal end (6) of the plunger (4) facing the bung (3) and aligned to receive light reflected by the bung (3).

21 Claims, 3 Drawing Sheets

Related U.S. Application Data continuation of application No. 14/761,769, filed as application No. PCT/EP2014/051470 on Jan. 27, 2014, now Pat. No. 9,878,099.

(51) Int. Cl.
| | |
|---|---|
| *G01D 5/32* | (2006.01) |
| *A61M 5/31* | (2006.01) |
| *A61M 5/145* | (2006.01) |
| *G01S 17/08* | (2006.01) |
| *A61M 5/315* | (2006.01) |

(52) U.S. Cl.
CPC ............... *G01D 5/34* (2013.01); *G01S 17/08* (2013.01); *A61M 5/31515* (2013.01); *A61M 2005/206* (2013.01); *A61M 2205/3306* (2013.01); *A61M 2205/587* (2013.01)

(58) Field of Classification Search
CPC ........ A61M 5/31515; A61M 2005/206; A61M 2205/587; A61M 2205/3306; G01S 17/08
See application file for complete search history.

(56) References Cited

U.S. PATENT DOCUMENTS

| | | | |
|---|---|---|---|
| 5,226,895 A | 1/1993 | Harris | |
| 5,273,187 A | 11/1993 | Suzuki | |
| 5,279,586 A | 1/1994 | Balkwil | |
| 5,304,152 A | 4/1994 | Sa | |
| 5,320,609 A | 6/1994 | Haber et al. | |
| 5,383,865 A | 1/1995 | Michel | |
| 5,433,712 A | 7/1995 | Stiles | |
| 5,480,387 A | 1/1996 | Gabrial et al. | |
| 5,505,704 A | 4/1996 | Dawelka et al. | |
| 5,582,598 A | 12/1996 | Chanoch | |
| 5,626,566 A | 5/1997 | Detersen et al. | |
| 5,674,204 A | 10/1997 | Chanoch | |
| 5,688,251 A | 11/1997 | Chanoch | |
| 5,700,247 A * | 12/1997 | Grimard ............... | A61M 5/315 604/220 |
| 5,792,117 A | 8/1998 | Brown | |
| 5,921,966 A | 7/1999 | Bendek et al. | |
| 5,927,957 A * | 7/1999 | Kennedy ................ | E03C 1/308 4/255.02 |
| 5,961,495 A | 10/1999 | Walters et al. | |
| 6,004,297 A | 12/1999 | Steenfeldt-Jensen et al. | |
| 6,027,481 A | 2/2000 | Barrelle et al. | |
| 6,065,270 A | 5/2000 | Reinhard et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,267,042 B1 | 7/2001 | Nagai | |
| 6,452,158 B1 | 9/2002 | Whatley | |
| 6,645,177 B1 | 11/2003 | Shearn | |
| 6,758,110 B1 * | 7/2004 | Takachi ............... | A61M 5/14566 74/89.39 |
| 6,899,698 B2 | 5/2005 | Sams | |
| 6,936,032 B1 | 8/2005 | Bush, Jr. et al. | |
| 7,241,278 B2 | 7/2007 | Moller | |
| 7,338,472 B2 | 3/2008 | Shearn | |
| 7,419,478 B1 | 9/2008 | Reilly | |
| 7,682,345 B2 | 3/2010 | Savage | |
| 8,545,478 B2 | 10/2013 | Gough et al. | |
| 9,435,666 B2 | 9/2016 | Richter | |
| 9,623,191 B2 * | 4/2017 | Uber, III ............... | A61M 5/007 |
| 2002/0052578 A1 | 5/2002 | Moller | |
| 2002/0120235 A1 | 8/2002 | Enggaard | |
| 2003/0050609 A1 | 3/2003 | Sams | |
| 2003/0125670 A1 | 7/2003 | Langley | |
| 2004/0059299 A1 | 3/2004 | Moller | |
| 2004/0064101 A1 | 4/2004 | Kowan et al. | |
| 2004/0103951 A1 | 6/2004 | Osborne | |
| 2004/0158205 A1 | 8/2004 | Savage | |
| 2004/0210199 A1 | 10/2004 | Atterbury et al. | |
| 2004/0260238 A1 * | 12/2004 | Call ................ | A61M 25/10182 604/97.03 |
| 2004/0267207 A1 | 12/2004 | Veasey et al. | |
| 2005/0015019 A1 * | 1/2005 | Honda ............ | A61B 5/150503 600/576 |
| 2005/0054979 A1 | 3/2005 | Liu | |
| 2005/0113765 A1 | 5/2005 | Veasey et al. | |
| 2006/0153693 A1 | 7/2006 | Flechter et al. | |
| 2006/0175427 A1 | 8/2006 | Jonientz et al. | |
| 2006/0229567 A1 | 10/2006 | Wright | |
| 2007/0270743 A1 | 11/2007 | Ackerman | |
| 2009/0137949 A1 | 5/2009 | Landau | |
| 2009/0275916 A1 | 11/2009 | Harms et al. | |
| 2009/0299279 A1 | 12/2009 | Richter | |
| 2010/0063447 A1 * | 3/2010 | Stempfle ............. | A61M 5/1456 604/151 |
| 2010/0262002 A1 | 10/2010 | Martz | |
| 2011/0004165 A1 * | 1/2011 | Iio .......................... | A61M 5/24 604/197 |
| 2012/0026874 A1 | 2/2012 | McEwen | |
| 2012/0139877 A1 | 6/2012 | Kawabe et al. | |
| 2012/0179112 A1 * | 7/2012 | Langley ............ | A61M 5/14566 604/228 |
| 2012/0265171 A1 * | 10/2012 | Thorne, Jr. ............. | A61M 5/19 604/518 |
| 2012/0268741 A1 | 10/2012 | Ponnnnereau | |
| 2013/0204224 A1 | 8/2013 | Muller-Pathle | |
| 2014/0194834 A1 * | 7/2014 | Passaglia ............ | A61M 1/0068 604/290 |
| 2014/0288408 A1 * | 9/2014 | Deutsch ............. | A61M 5/31511 600/407 |
| 2015/0051546 A1 * | 2/2015 | Weiss .................. | A61M 5/1452 604/121 |
| 2015/0080790 A1 * | 3/2015 | Munk ............... | A61M 5/14566 604/67 |

FOREIGN PATENT DOCUMENTS

| | | |
|---|---|---|
| CN | 1671432 | 9/2005 |
| CN | 1876191 | 12/2006 |
| CN | 101175519 | 5/2008 |
| CN | 101454032 | 6/2009 |
| CN | 101522239 | 9/2009 |
| CN | 101801442 | 8/2010 |
| CN | 101868179 | 10/2010 |
| CN | 101909673 | 12/2010 |
| CN | 102591453 | 7/2012 |
| EP | 0916353 | 5/1999 |
| EP | 0937471 | 8/1999 |
| EP | 0937476 | 8/1999 |
| JP | 2004-194802 | 7/2004 |
| JP | 2010-160114 | 7/2010 |
| JP | 2011-20003 | 8/2012 |
| WO | WO 99/38554 | 8/1999 |
| WO | WO 01/10484 | 2/2001 |
| WO | WO 02/04049 | 1/2002 |
| WO | WO 02/083209 | 1/2002 |
| WO | WO 2002/00409 | 1/2002 |
| WO | WO 2002/056934 | 7/2002 |
| WO | WO 2004/009163 | 1/2004 |
| WO | WO 2005/004956 | 1/2005 |
| WO | WO 2006/124819 | 11/2006 |
| WO | WO 2007/132353 | 11/2007 |
| WO | WO 2009/083600 | 7/2009 |
| WO | WO 2009/036496 | 10/2009 |
| WO | WO 2011/032960 | 3/2011 |
| WO | WO 2011/099551 | 8/2011 |

OTHER PUBLICATIONS

English Translation of Notice of Reasons for Rejection issued in Japanese Patent Application No. 2015-554167, dated Oct. 24, 2017, 5 pages.
International Search Report and Written Opinion in International Application No. PCT/EP2014/051470, dated May 2, 2014, 3 pages.

(56) References Cited

OTHER PUBLICATIONS

International Preliminary Report on Patentability in International Application No. PCT/EP2014/051470, dated Aug. 4, 2015, 6 pages.

* cited by examiner

ARRANGEMENT FOR DETECTING A POSITION OF A PLUNGER

CROSS REFERENCE TO RELATED APPLICATIONS

The present application is a continuation of U.S. patent application Ser. No. 15/877,920, filed Jan. 23, 2018, which is a continuation of U.S. patent application Ser. No. 14/761,769, filed Jul. 17, 2015, now U.S. Pat. No. 9,878,099, which is a U.S. National Phase Application pursuant to 35 U.S.C. § 371 of International Application No. PCT/EP2014/051470, filed Jan. 27, 2014, which claims priority to European Patent Application No. 13153137.8, filed Jan. 29, 2013. The entire disclosure contents of these applications are herewith incorporated by reference into the present application.

TECHNICAL FIELD

The invention relates to an arrangement for detecting a position of a plunger relative to a bung in a drug cartridge.

BACKGROUND OF THE INVENTION

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring. In other devices this is achieved by an electromechanical drive. Devices with electromechanical and/or electronic components may comprise a drive for electrically displacing a bung within the cartridge or syringe.

WO 02/083209 A1 discloses a pump system for an infusion system including a linear drive which minimizes the space occupied by the pump system in a portable housing. A motor and a motor drive shaft are arranged in parallel with, and adjacent to a syringe and lead screw. A gear box connects the drive shaft and lead screw to transfer rotational movements between them. A piston driving member, such as a cone or drive nut converts the rotational movement of the lead screw into linear motion of a syringe piston. Sensors detect when the piston or cone is in a "home" position and in an "end" position, respectively. A clamping member selectively clamps the lead screw against linear motion in at least a dispensing direction. Optionally, a proximity sensor is used to ensure that the cone and the pistonare abutting during dispensing.

SUMMARY OF THE INVENTION

It is an object of the present invention to provide an improved arrangement for detecting a position of a plunger relative to a bung in a drug cartridge.

The object is achieved by an arrangement for detecting a position of a plunger relative to a bung in a drug cartridge according to claim 1.

Preferred embodiments of the invention are given in the dependent claims.

According to the invention an arrangement for detecting a position of a plunger relative to a bung in a drug cartridge, comprises a proximity sensor located close to a distal end of the plunger facing the bung and aligned to receive light reflected by the bung.

In order to accommodate manufacturing tolerances of bung positions within cartridges drug delivery devices position a home or start position of their plungers in axial clearance from a proximal face of the bung. Before injection doses can be taken it is advisable to position the plunger directly into contact with the bung. It is also possible for a user to insert a partially used cartridge into the drug device. In both cases it is advantageous for the drug delivery device to be able to determine the position of the bung relative to the plunger in order to be able to automatically position the plunger in a position where priming can be performed. This is achieved by the arrangement according to the invention. The plunger may be advanced towards the bung while the proximity sensor receives light reflected from the bung thus determining whether the plunger has made contact with the bung or not.

According to the invention the proximity sensor is arranged as an imaging sensor located close to a distal end of the plunger facing the bung and aligned to image the bung, wherein the bung comprises a compliant material and has a substantially flat proximal face with a resilient surface structure protruding from the flat proximal face and adapted to deform on contact with the plunger. The distal end may be covered by a transparent plate, and the imaging sensor may be located behind the transparent plate. The transparent plate may protect the imaging sensor from environmental conditions, such as humidity, dust and/or the like. Alternatively, the distal end of the plunger is open without any protection of the imaging sensor.

As the surface structure is arranged to deform when contacting the plunger, the proximity sensor will detect different images depending on whether the plunger contacts the bung or not. The images from the proximity sensor are processed to determine the first presence of the protruding surface structure of the bung in contact with the plunger. As soon as this condition is met the plunger can be stopped.

In an exemplary embodiment the proximity sensor comprises a light source and a light sensor. Likewise the proximity sensor can be of any type suitable for imaging. Furthermore, the proximity sensor may comprise a lens for mapping an image of the bung onto the sensor.

In an exemplary embodiment the flat proximal face of the bung is circular and the surface structure comprises four elongate protrusions equally spaced around the flat proximal face. The elongate protrusions may for example be directed in a radial or tangential direction with respect to the circular flat proximal face.

In another exemplary embodiment the surface structure comprises two concentric circles. In yet another exemplary embodiment the surface structure comprises a cross. In yet another exemplary embodiment the flat proximal face is circular and the surface structure comprises eight small circular protrusions equally spaced around the circular flat proximal face.

In another exemplary embodiment the light source and the light sensor are arranged in compartments within the plunger which are optically isolated from each other such that light emitted from the light source is prevented from directly illuminating the light sensor. Prior to contact of the plunger with the bung light is emitted from the light source, reflected by the bung and received by the light sensor. On contact with the bung light from the compartment of the light source cannot be reflected into the compartment of the light sensor thus providing a simple means for detecting contact of the plunger with the bung. In this embodiment the light sensor does not have to be an imaging sensor. Instead, the light sensor can for example be arranged as a light sensitive resistor.

In an exemplary embodiment a processing unit for processing images acquired by the proximity sensor is integrated with the proximity sensor or arranged as an additional device.

The proximity sensor may be connected to the processing unit and/or another electronic device such as a control unit of a drug delivery device by a cable arranged within the plunger.

In an exemplary embodiment the distal end of the plunger is substantially flat. In another exemplary embodiment the distal end of the plunger is arranged as the lens of the proximity sensor. This may simplify the optics and the manufacturing and thus reduce costs.

The arrangement may be part of a drug delivery device, comprising a drug cartridge with a bung, a plunger for displacing the bung, an electromechanical drive for displacing the plunger and an arrangement for detecting a position of the plunger relative to the bung according to the invention.

A control unit may be arranged in the drug delivery device for causing the electromechanical drive to advance the plunger towards the bung and stop the electromechanical drive if the proximity sensor detects an image of the bung indicating contact with the plunger differing from an image prior to contact between the bung and the plunger.

This allows the drug delivery device to determine the position of the bung relative to the plunger in order to be able to automatically position the plunger in a position where priming can be performed prior to an injection.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION OF PREFERRED EMBODIMENTS

Figure 1:
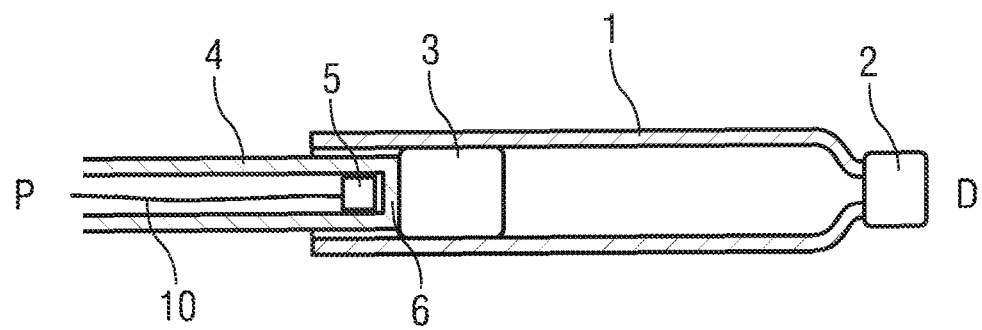
FIG. 1 is a schematic longitudinal detail section of an exemplary embodiment of a drug cartridge with an arrangement for detecting a position of a plunger.

FIG. 1 is a schematic longitudinal detail section of an exemplary embodiment of a drug cartridge 1 or syringe with a septum 2 or discharge nozzle at a distal end and a bung 3 or stopper disposed within the cartridge 1 near a proximal end. A plunger 4 is arranged for displacing the bung 3 within the cartridge 1 for dispensing the drug contained within the cartridge 1.

A proximity sensor 5 arranged as an imaging sensor is disposed within the plunger 4. The proximity sensor 5 can be of any type suitable for imaging, but preferentially may be of the type comprising a light source, light sensor, lens and processing unit. The proximity sensor 5 is located close to a flat transparent distal end 6 of the plunger 4 facing the bung 3 and aligned to image the bung 3.

Figure 2:
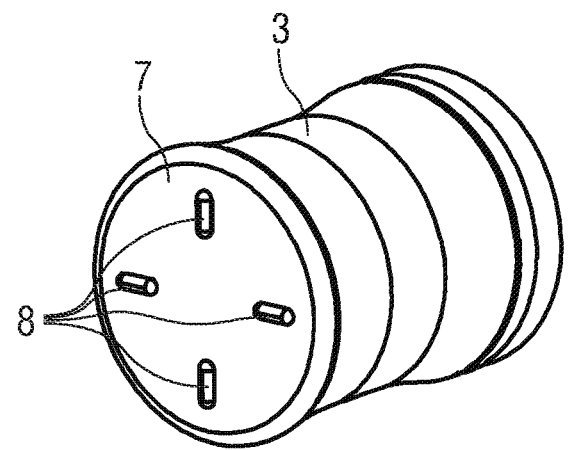
FIG. 2 is a schematic perspective view of an exemplary embodiment of a bung.

FIG. 2 is a schematic perspective view of an exemplary embodiment of the bung 3. In this embodiment the bung 3 consists of or comprises a compliant material and has a substantially flat proximal face 7 with a surface structure 8 protruding from the flat proximal face 7. In the illustrated embodiment the surface structure 8 comprises four small elongate protrusions ('pip' features) equally spaced around the circular flat proximal face 7 and directed in a radial direction. The surface structure 8 is arranged to deform when contacting the plunger 4. The proximity sensor 5 will therefore detect different images depending on whether the plunger 4 contacts the bung 3 or not.

Figure 3:
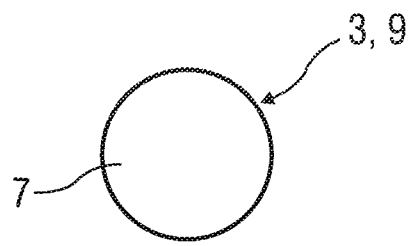
FIG. 3 is an exemplary embodiment of an image of a flat proximal face of the bung acquired by a proximity sensor prior to contact of a plunger with the bung.

FIG. 3 is an exemplary embodiment of the image 9 acquired by the proximity sensor 5 prior to contact of the plunger 4 with the bung 3. The surface structure 8 is not detected.

Figure 4:
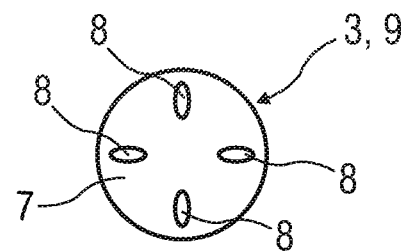
FIG. 4 is an exemplary embodiment of an image of the flat proximal face of the bung acquired by the proximity sensor on to contact of the plunger with the bung.

FIG. 4 is an exemplary embodiment of the image 9 acquired by the proximity sensor 5 on contact of the plunger 4 with the bung 3. The surface structures 8 are detected.

Figure 5:
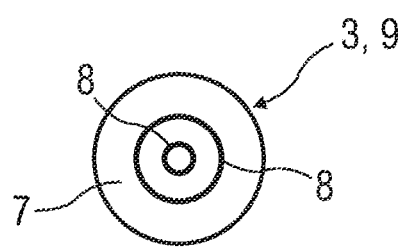
FIG. 5 is an image of the flat proximal face of the bung with an alternative surface structure.
Figure 6:
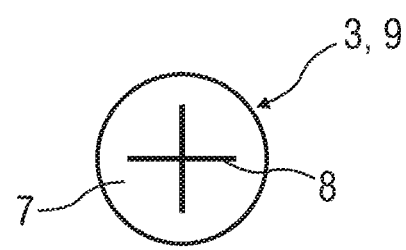
FIG. 6 is an image of the flat proximal face of the bung with an alternative surface structure
Figure 7:
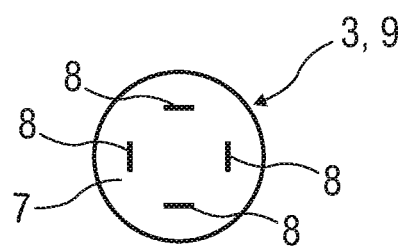
FIG. 7 is an image of the flat proximal face of the bung with an alternative surface structure.
Figure 8:
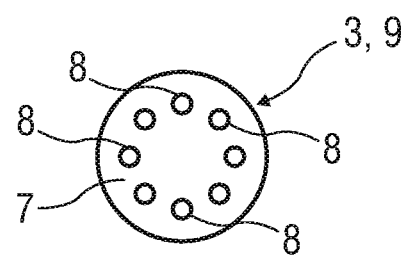
FIG. 8 is an image of the flat proximal face of the bung with an alternative surface structure.

FIGS. 5 to 8 are alternative exemplary embodiments of images 9 of the flat proximal face 7 of the bung 3 with the surface structure 8. In the embodiment of FIG. 5 the surface structure 8 comprises two concentric circles. In the embodiment of FIG. 6 the surface structure 8 comprises a cross. In the embodiment of FIG. 7 the surface structure comprises four small elongate protrusions equally spaced around the circular flat proximal face 7 and tangentially aligned. In the embodiment of FIG. 8 the surface structure comprises eight small circular protrusions equally spaced around the circular flat proximal face 7.

The processing unit may be integrated with the proximity sensor 5 or arranged as an additional device. The proximity sensor 5 may be connected to the processing unit and/or other electronic equipment by a cable 10 arranged within the plunger 4.

The cartridge 1 and plunger 4 may be part of a drug delivery device (not illustrated). The drug delivery device may comprise a body adapted to receive the cartridge 1. A hypodermic needle may be attached to the cartridge 1, preferably a needle with two tips, one of them for piercing an injection site and the other for piercing the septum 2 on the cartridge 1 for establishing a fluid communication between the cartridge 1 and the needle. The drug delivery device may further comprise at least one electric unit or electronic device (not illustrated) such as a control unit and/or a human-machine-interface for communicating information to a user and for allowing the user to operate the drug delivery device and an electromechanical drive (not illustrated) for inserting the needle into an injection site, e.g. a patient's skin and/or dispensing drug from the cartridge 1 through the needle and/or retracting the needle post-injection. The electromechanical drive may comprise motor driven gear boxes driving simple power screws or telescopic power screws.

In order to properly position the plunger 4 at the bung 3 prior to dispensing the drug the plunger 4 is driven towards the bung 3 with the proximity sensor 5 actively imaging. Images 9 from the proximity sensor 5 are processed to determine the first presence of the protruding surface structure 8 of the bung 3 in contact with the plunger 4. As soon as this condition is met the plunger 4 is stopped.

In an exemplary embodiment the transparent distal end 6 of the plunger 4 may not be flat but arranged as a lens for the proximity sensor 5. This may simplify the optics and the manufacturing and thus reduce costs.

Figure 9:
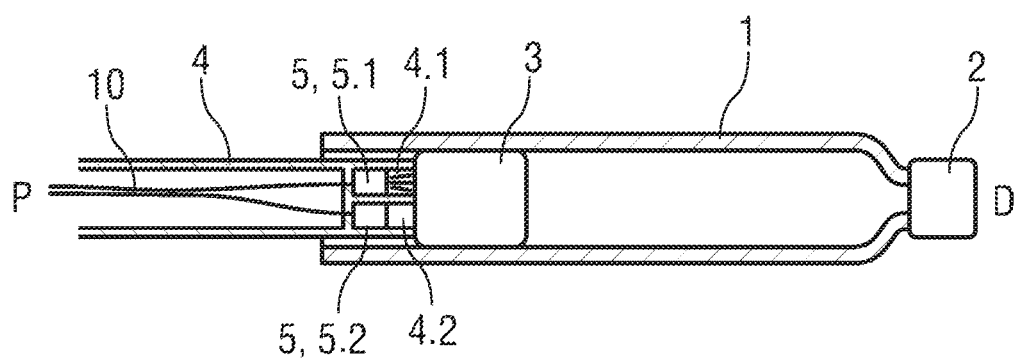
FIG. 9 is a schematic longitudinal detail section of another exemplary embodiment of a drug cartridge with an arrangement for detecting a position of a plunger.

FIG. 9 is a schematic longitudinal detail section of an exemplary embodiment of a drug cartridge 1 or syringe with a septum 2 or discharge nozzle at a distal end and a bung 3 or stopper disposed within the cartridge 1 near a proximal end. A plunger 4 is arranged for displacing the bung 3 within the cartridge 1 for dispensing the drug contained within the cartridge 1.

A proximity sensor 5 comprising a light source 5.1, e.g. a light emitting diode, and a light sensor 5.2, e.g. a light sensitive resistor, is disposed within the plunger 4.

The light source 5.1 and the light sensor 5.2 are arranged in compartments 4.1, 4.2 within the plunger 4 which are optically isolated from each other such that light emitted from the light source 5.1 cannot directly illuminate the light sensor 5.2.

The compartments 4.1, 4.2 are open at the distal end of the plunger 4 facing the bung 3.

A processing unit may be integrated with the proximity sensor 5 or arranged as an additional device. The proximity sensor 5 may be connected to the processing unit and/or other electronic equipment by a cable 10 arranged within the plunger 4.

Prior to contact with the bung 3, light emitted from the light source 5.1 is reflected by the bung 3 and detected by the light sensor 5.2. At the point where the plunger contacts the surface of the bung 3, both compartments are covered over and optically isolated from each other. At this point light is no longer received at the light sensor 5.2. This enables detection of contact between the plunger 4 and the bung 3, e.g. by means of the processing unit. Thus, when the light detected by the light sensor 5.2 is below a threshold, the processing unit determines that contact between the plunger 4 and the bung 3 is made, for example by detecting that a signal level of an electrical signal generated by the light sensor 5.2 is below a predetermined threshold.

In order to properly position the plunger 4 at the bung 3 prior to dispensing the drug the plunger 4 is driven towards the bung 3 with the proximity sensor 5 receiving light. Responses from the proximity sensor 5 are processed to determine the first contact of the bung 3 with the plunger 4. As soon as this condition is met the plunger 4 is stopped.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu- Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES 1 cartridge
2 septum
3 bung
4 plunger
4.1 compartment
4.2 compartment
5 proximity sensor
5.1 light source
5.2 light sensor
6 transparent distal end
7 flat proximal face
8 surface structure
9 image
10 cable
D distal direction
P proximal direction

The invention claimed is:
1. A medical device comprising:
a drug cartridge comprising a bung;
a proximity sensor located within a hollow plunger close to a distal end of the hollow plunger facing the bung and aligned to receive light reflected by the bung, wherein the received reflected light is used to detect a position of the hollow plunger relative to the bung in the drug cartridge of the medical device; and
a control unit arranged to cause an electromechanical drive to advance the hollow plunger towards the bung and to cause the electromechanical drive to stop the hollow plunger from advancing towards the bung if the proximity sensor detects a first image of the bung indicating a contact between the bung and the hollow plunger differing from a second image prior to the contact between the bung and the hollow plunger.
2. The medical device of claim 1, wherein the hollow plunger is movable between a home position and a proximal face of the bung, and wherein the home position of the hollow plunger in the medical device is positioned in axial clearance from the proximal face of the bung.
3. The medical device of claim 1, wherein the proximity sensor comprises a light source and a light sensor.
4. The medical device of claim 3, wherein the light source is arranged in a first compartment and the light sensor is arranged in a second compartment.

5. The medical device of claim 4, wherein the first compartment and the second compartment are attached to the hollow plunger.

6. The medical device of claim 5, wherein the first compartment and the second compartment are optically isolated from each other such that light emitted from the light source is prevented from directly illuminating the light sensor.

7. The medical device of claim 1, wherein the proximity sensor comprises a lens.

8. The medical device of claim 1, wherein a proximal face of the bung is substantially flat and is circular.

9. The medical device of claim 8, wherein a surface structure of the bung comprises a plurality of elongate protrusions equally spaced around the proximal face.

10. The medical device of claim 1, wherein a surface structure of the bung comprises a plurality of concentric circles.

11. The medical device of claim 1, wherein a surface structure of the bung comprises a cross.

12. The medical device of claim 1, wherein a surface structure of the bung comprises a plurality of circular protrusions equally spaced around a substantially flat and circular proximal face of the bung.

13. The medical device of claim 1, wherein the distal end of the hollow plunger is covered by a transparent plate.

14. The medical device of claim 13, wherein the proximity sensor comprises a light sensor that is located behind the transparent plate.

15. The medical device of claim 1, further comprising a processing unit configured to process images acquired by the proximity sensor.

16. The medical device of claim 15, wherein the processing unit is integrated with the proximity sensor.

17. The medical device of claim 15, wherein the proximity sensor is connected to the processing unit by a cable arranged within the hollow plunger.

18. The medical device of claim 1, wherein the distal end of the hollow plunger is arranged as a lens of the proximity sensor.

19. A drug delivery device comprising:
a drug cartridge with a bung;
a hollow plunger configured to displace the bung;
an electromechanical drive configured to displace the hollow plunger;
a proximity sensor located within a distal end of the hollow plunger facing the bung and aligned to receive light reflected by the bung, wherein the received reflected light is used to detect a position of the hollow plunger relative to the bung in the drug cartridge; and
a control unit arranged to cause the electromechanical drive to advance the hollow plunger towards the bung and to cause the electromechanical drive to stop the hollow plunger from advancing towards the bung if the proximity sensor detects a first image of the bung indicating a contact between the bung and the hollow plunger differing from a second image prior to the contact between the bung and the hollow plunger.

20. The drug delivery device of claim 19, wherein the hollow plunger is cylindrical.

21. The medical device of claim 1, wherein the hollow plunger is cylindrical.

* * * * *